United States Patent
Wu et al.

[11] Patent Number: 5,811,121
[45] Date of Patent: Sep. 22, 1998

[54] PH-SENSITIVE COATINGS BASED ON CELLULOSE ACETOACETATE

[75] Inventors: Stephen Hong-Wei Wu; Chung-Ming Kuo, both of Kingsport, Tenn.

[73] Assignee: Eastman Chemical Company, Kingsport, Tenn.

[21] Appl. No.: 790,644

[22] Filed: Jan. 29, 1997

[51] Int. Cl.[6] .................................................. A61K 9/28
[52] U.S. Cl. .......................... 424/468; 424/465; 424/474
[58] Field of Search ................................... 424/468, 465, 424/474

[56] References Cited

U.S. PATENT DOCUMENTS

| | | | |
|---|---|---|---|
| 2,500,029 | 4/1950 | Hagemeyer | 260/225 |
| 2,521,897 | 4/1950 | Caldwell | 260/225 |
| 3,908,045 | 9/1975 | Alterman et al. | 424/403 |
| 3,944,497 | 3/1976 | Alterman et al. | 252/96 |
| 3,983,254 | 9/1976 | Alterman et al. | 252/96 |
| 4,078,099 | 3/1978 | Mazzola | 427/213 |
| 4,124,734 | 11/1978 | Alterman et al. | 252/187 |
| 4,126,717 | 11/1978 | Mazzola | 427/220 |
| 4,136,052 | 1/1979 | Mazzola | 252/99 |
| 4,762,637 | 8/1988 | Aronson et al. | 252/99 |
| 5,000,869 | 3/1991 | Dittert | 252/102 |
| 5,292,783 | 3/1994 | Buchanan et al. | 524/37 |
| 5,446,079 | 8/1995 | Buchanan et al. | 524/41 |
| 5,521,304 | 5/1996 | Edgar et al. | 536/115 |
| 5,559,171 | 9/1996 | Buchanan et al. | 524/41 |
| 5,580,911 | 12/1996 | Buchanan et al. | 524/41 |

*Primary Examiner*—Thurman K. Page
*Assistant Examiner*—Kathryne E. Shelborne
*Attorney, Agent, or Firm*—Andrew B. Griffis; Harry J. Gwinnell

[57] ABSTRACT

This invention is based on the discovery that certain cellulose acetoacetate mixed esters will remain insoluble in mild (near-neutral) or acidic aqueous solutions, but dissolve under alkaline conditions. The esters are particularly useful as coatings for controlled-release applications. Coatings comprising these esters will dissolve to release a coated active agent under alkaline conditions, the exact pH at which dissolution occurs being adjustable.

18 Claims, 1 Drawing Sheet

PH-SENSITIVE COATINGS BASED ON CELLULOSE ACETOACETATE

FIELD OF THE INVENTION

The present invention relates to pH-sensitive coatings comprising cellulose acetoacetate esters. The coatings are useful in applications requiring controlled release of active agents.

BACKGROUND OF THE INVENTION

Controlled release of active agents into selected environments is an area of intense study. Active agents include, for example, medicaments, pesticides, herbicides, catalysts, cosmetics, laundry products, colorants, and other materials. Various effort have been made in the past to incorporate such agents into a film-forming or matrix material that dissolves at an appropriate time to release the active agent. For instance, encapsulation of bleaching agents with pH-sensitive coatings from non-aqueous solutions of fatty acids is described by Alterman et al. in U.S. Pat. Nos. 3,908,045, 3,944,497, 3,983,254, and 4,124,734. Non-aqueous or solvent-borne coatings, however, are being replaced by water-borne coatings and other new technologies due to environmental concerns.

Mazzola describes the use of molten fatty acid-containing coatings in U.S. Pat. Nos. 4,078,099, 4,126,717, and 4,136,052. Fatty acids, oils, and waxes are unsuitable for many applications because they tend to cause enhanced foaming.

Aronson et al. teaches the use of pH-sensitive coatings of copolymers from carboxylic acids, carboxylic anhydrides, alkyl partial esters thereof, and their salt derivative in U.S. Pat. No. 4,762,637. These materials are also unsuitable for many purposes since they tend to persist in the environment.

Cellulose-based materials are particularly attractive candidates for use as coating material, since cellulose is so abundant, and some esters thereof have been shown to be biodegradable. See, for instance, Buchanan et al., U.S. Pat. Nos. 5,580,911, 5,559,171, 5,446,079, and 5,292,783.

The use of cellulose esters for pH-sensitive controlled-release coatings under acidic environments is well known and widely practiced. Such known materials include mixed esters such as cellulose propionate morpholinobutyrate (CPMB), cellulose acetate trimellitate (CAT), and cellulose acetate phthalate (CAP). The ability of a coating to control release under alkaline conditions, however, is not well-known.

Dittert, U.S. Pat. No. 5,000,869, describes the use of enteric polymers such as cellulose acetate phthalate, hydroxypropyl methycellulose phthalate, and polyvinyl acetate phthalate for encapsulation of tetrachloroglycoluril, a bleaching and cleaning agent. These coatings are said to dissolve at from mild (near-neutral) to alkaline conditions. However, phthalated enteric polymers, such as cellulose acetate phthalate, can break down to yield free phthalic acid when stored in contact with moisture. In doing so, their pH-sensitivity is diminished or lost, and in some cases, the polymer becomes totally insoluble in aqueous buffers. A similar problem also exists with cellulose esters containing the trimellityl moiety. Therefore, when long-term storage stability is desirable, such materials are not preferred as coatings.

In certain applications it would be desirable to have release coatings that will enable medicaments and other active agents to be delivered to alkaline environments without the above mentioned problems. For instance, in the pharmaceutical field, often it is desirable to deliver medicaments through the acidic environment of the stomach to another target site of absorption or action.

As a specific example, the target site of 5-aminosalycilic acid (5-ASA) is the large intestine area. In the human digestive system, the pH of the stomach varies from about 1 to about 3.5, the pH of the small intestine may range from about 4–7, and the pH of the large intestine is about 7.5–8. Thus it would be desirable to have a coating that could resist the acidic and mild or near-neutral environments of the stomach and small intestine, but dissolve under the alkaline conditions of the large intestine.

There are few references to cellulose esters containing the acetoacetate moiety (C(AA)Es). U.S. Pat. No. 2,500,029, to Hagemeyer, discloses treatment of fibers spun from cellulose acetoacetate (CAA) with formaldehyde in the presence of pyridine to give fibers insoluble in acetone. U.S. Pat. No. 2,521,897, to Caldwell, describes a method of synthesis for CAA and mentions that is can be cast into a film.

More recently, Edgar et al., U.S. Pat. No. 5,521,304, teach a new route to cellulose acetoacetate esters. Furthermore, it was found that certain cellulose acetoacetate esters having a total degree of substitution per anhydroglucose unit (DS/AGU) of 0.1 to 1.0 are water-soluble and, when crosslinked, provide an excellent coating material for substrates such as paper, polymer films, metals, painted substrates, and the like. This reference is incorporated by reference in its entirety.

However, none of the aforementioned references suggest a stable, cellulose-based coating, for medicaments and other active agents, having pH-dependent solubility characteristics for controlled-release into alkaline environments. Thus, a coating material comprising a cellulose acetoacetate ester that is insoluble in water under mild (about pH=7) or acidic conditions and yet which is readily soluble under alkaline conditions, and which is stable against decomposition in the presence of incidental moisture, would provide an important advance in the area of controlled release coatings for use in alkaline environments.

SUMMARY OF THE INVENTION

The present inventors have discovered that cellulose acetoacetate esters (C(AA)Es) having a second and different ester moiety can be designed to be soluble only under alkaline conditions and are effective as a coating to protect the coated material at mild (near neutral) or acidic conditions. Such coatings will dissolve under more alkaline conditions to release the coated material. The pH above which the coating dissolves can be adjusted by proper selection of the second ester group, the degree of substitution and the polymer chain length, so that the characteristic pH of the cellulose acetoacetate ester can be adjusted to virtually any pH above about 7 to about 11.

Accordingly, an object of the present invention is to describe coatings having the cellulose backbone and containing the acetoacetate moiety and a second ester moiety, which are insoluble in aqueous media at mild (about pH=7) to acidic conditions and yet which readily dissolve in aqueous media when the pH becomes alkaline.

Another object of the invention is to describe cellulose acetoacetate esters that are readily formed into films, and thus are useful as coatings, either as flat films or as encapsulating agents, wherein the coatings protect the active agent for delivery to highly alkaline conditions, such as pH=9 and above.

A further object of the invention is to describe coatings comprising cellulose acetoacetate esters that dissolve under alkaline conditions, and not before, and yet do not contain free carboxyl pendant groups, as in the known enteric coatings, nor do they contain the unstable phthalyl or trimellityl groups.

Yet another object of the invention is to describe cellulose acetoacetate esters that can be used as a matrix system, where the active ingredient(s) or material to be protected are finely dispersed in the polymer matrix, and wherein the matrix system has a characteristic pH under alkaline conditions.

Still another object of the invention is to describe a coating or mixed coatings comprising the cellulose acetoacetate ester according to the present invention that may be designed to enable a coating to dissolve at a wide variety of pHs.

DETAILED DESCRIPTION OF THE INVENTION

Figure 1:
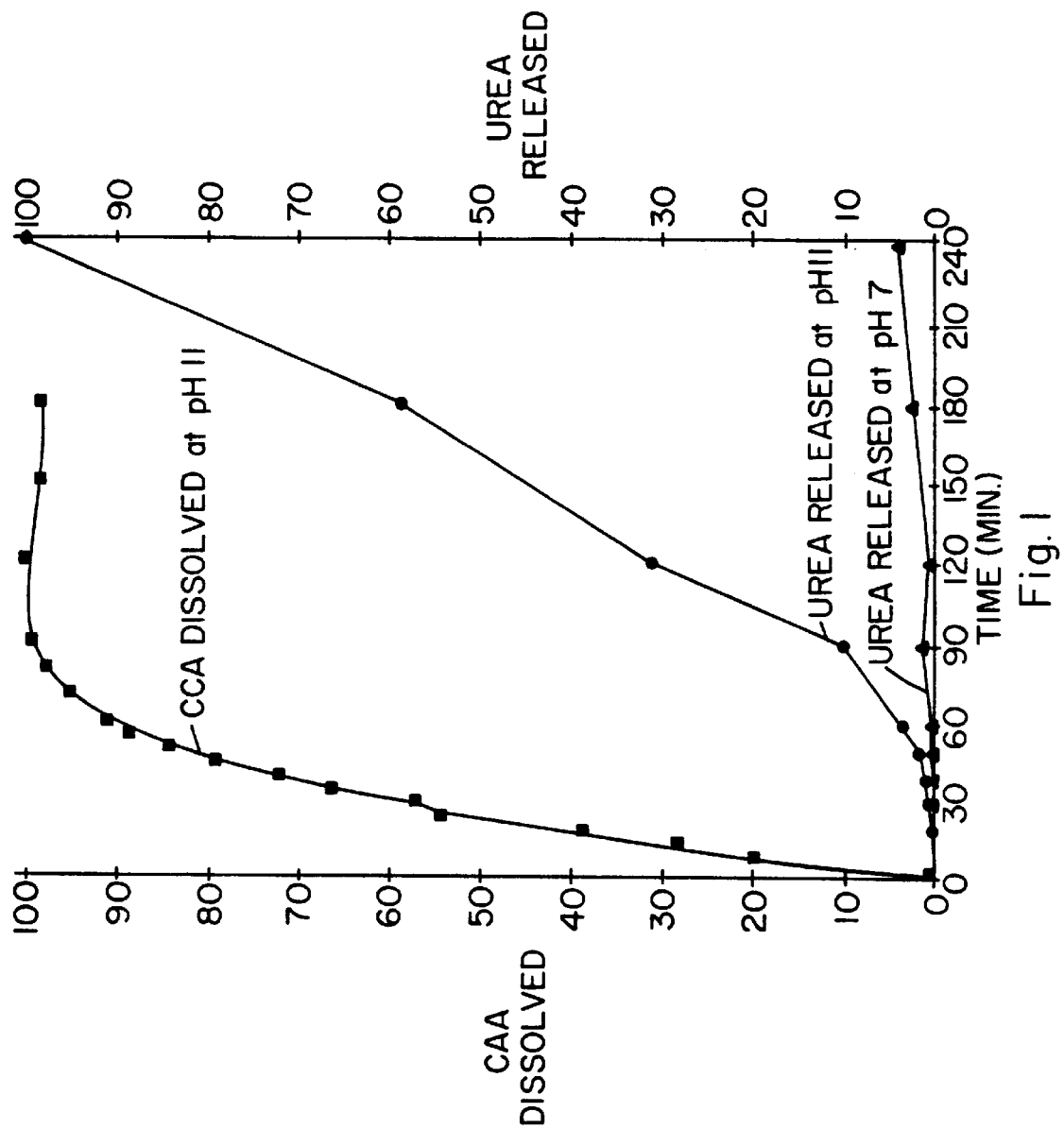
FIG. 1 is a graph showing time-dependent dissolution of a cellulose acetate acetoacetate according to one embodiment of the present invention, at pH=11 (top curve), and the detection of dissolved coated urea prills at pH=11 and pH=7 (bottom two curves, respectively), the urea being coated with a coating according to an embodiment of the present invention.

The present invention relates to cellulose esters having the formula:

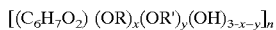

$$[(C_6H_7O_2)(OR)_x(OR')_y(OH)_{3-x-y}]_n$$

where $(C_6H_7O_2)$ is the basic cellulose backbone, being essentially anhydroglucose units joined by an oxygen linkage to form long molecular chains, R represents a $C_2$–$C_4$ acyl-containing aliphatic group, and OR' is the acetoacetate moiety, —O—C(O)—CH$_2$—C(O)—CH$_3$.

As mentioned, R is selected from $C_2$–$C_4$ acyl-containing groups. R is preferably acetyl, propionyl, or butyryl, most preferably acetyl. The precise pH of dissolution of the cellulose ester is affected by the selection of R, as well as by the selection of x, y, and n.

The degree of substitution per anhydroglucose unit (DS/AGU) is represented by x for the OR group, y for the acetoacetate group. The residual hydroxyl groups can be calculated from (3-x-y). The total degree of substitution is represented by x+y. Of course it is to be understood that x, y, and (3-x-y) represent the average degree of substitution over the entire polymer.

The degree of substitution for the ester, represented by x, can range from about 0.25 to about 2.0, preferably about 0.5 to about 1.5, and most preferably about 1.1 to about 1.5. The degree of substitution of acetoacetate, represented by y, can range from about 0.5 to about 2.75, preferably about 1.0 to about 2.5, and most preferably about 1.1 to about 1.7.

It is preferred but not essential that number of hydroxyl groups per anhydroglucose unit remaining in the polymer be in the range of about 0.25 to about 0.75.

The total degree of substitution (DS/AGU), defined as x+y or the sum of the degree of substitution of acetoacetyl and the $C_2$–$C_4$ acyl-containing aliphatic group, is about 0.75 to fully substituted (3.0), more preferably greater than about 1.0, even more preferably about 1.1 to about 2.75, and most preferably about 2.2 to about 2.75.

The molecular weight is not particularly critical. The cellulose chain length has a greater impact on processability and/or film-forming ability than on solubility in aqueous alkaline solution. Generally when n is too low, the film-forming qualities of the cellulose acetoacetate mixed ester is poor, and when n is too high (greater than about 400), the cellulose acetoacetate mixed ester according to the present invention is difficult to process. For an uncrosslinked cellulose acetoacetate ester, soluble in aqueous alkaline solution, easy to process, and possessing good film-forming characteristics, generally n should be greater than about 50 and less than 400. More preferably it has been found that a cellulose acetoacetate ester having a weight average molecular weight (as measured by gel permeation chromatography in 1-methyl-2-pyrrolidinone using polystyrene standards), $M_w$, of about 20,000 to about 200,000 or even more preferably greater than 20,000 to about 120,000, affords particularly useful coatings.

The term "soluble" as used herein means soluble at least to the extent as defined in the Handbook of Chemistry and Physics, 56th Edition, CRC Press, Cleveland, Ohio (1975–1976), pg. C-56, paragraph 11, or as otherwise set forth below in specific examples. The term "insoluble" is as defined in the aforementioned reference. The term "readily soluble" as used herein means the designated material or composition dissolves at a rate which is effective for the intended use, i.e., so that a coating dissolves under alkaline conditions so that an active agent, such as a medicament or colorant or cleaning agent, is delivered to the target site. The term "dissolves" as used herein means that the designated material will form a solution in the designated solvent (which will be water for the purposes of the present invention, unless otherwise stated).

Preparation of the cellulose acetoacetate esters.

There are several known methods of preparing cellulose acetoacetate esters. A good review of the known methods, as well as a novel new route, is found in the aforementioned Edgar et al. reference. Cellulose acetate acetoacetate (or the corresponding propionate or butyrate acetoacetate esters) can generally be prepared by reacting cellulose or cellulose acetate with acetoacetylation agents such as diketene, t-butyl acetoacetate, and diketene/acetone adduct (2,2,6trimethyl-4H-1,3,dioxnin-4-one).

More specifically, they may be prepared by reaction of cellulose acetate having various degrees of acetate content (<3 DS/AGU) with the above acetoacetylation agents (diketene, etc.). The degree of substitution for acetate (or in general the R group) is controlled by the starting cellulose acetate used, the amount of the acetoacetylation agent used, the reaction time and the reaction temperature. The acetoacetyl group preferentially substitutes for the hydroxyl groups on the basic cellulose backbone.

Alternatively, the esters used in the present invention may be derived by reacting cellulose with the above acetoacetylation agent, then with acetic anhydride, or acetic anhydride first then acetoacetylation agent. In this case, the degree of substitutions are controlled by the amount of anhydride and acetoacetylation agent used, and reaction temperature and reaction time. The total substitution can also be controlled by removing some acetate and/or acetoacetate by hydrolysis of the above reaction products. In a further variation, cellulose in a solution such as LiCl/dimethyl acetamide may be reacted with the acylation agents in the same manner.

The skilled artisan in possession of the present disclosure is fully capable of preparing the cellulose acetoacetate esters of the invention without more than routine experimentation.

The cellulose acetoacetate esters used in the coatings according to the present invention are not crosslinked, and have a higher total DS/AGU than the water-soluble material taught in Edgar et al., cited above.

Coating process using the cellulose ester of the invention

A particular active ingredient, such as a medicament, nutrient, pesticide, and the like, may be encapsulated or dispersed within a coating or a matrix comprising the cellulose acetoacetate esters according to the present invention. It is generally well-known how to encapsulate or disperse medicaments with a layer of continuous coating materials or within a matrix. See, for instance, "Microencapsulation and Related Process", by Patrick Deasy, Marcel Dekker, New York, N.Y. (1984), and "The Theory and Practice of Industrial Pharmacy", by Lachman, et al., Lea and Febuger, Philadelphia (1970). Any coating process known in the art may be used to coat the cellulose acetoacetate esters according to the present invention.

Furthermore, the coating thickness may be varied by per se known methods, which will also alter the dissolution time and is a further contemplated modification of the present invention. Likewise, more than one active agent may be encapsulated at the same time and more than one coating may be used, e.g., a mixed coating comprising a cellulose acetate acetoacetate ester and an enteric polymer as discussed previously, may be prepared. In addition, the active agent may be encapsulated by more than one coating, e.g., a first (or second) coating of cellulose acetate acetoacetate and a second (or first) coating of an enteric polymer. It is within the capability of the skilled artisan in possession of the present disclosure to encapsulate or form a matrix composition with active agents, using the cellulose acetoacetate mixed ester according to the present invention, without undue experimentation.

Other polymeric materials that can be mixed with polymers according to the present invention may be found in "Materials Used in Pharmaceutical Formulations", edited by A. T. Florence, Blackwell Scientific Pub., Oxford, London (1984) and "Polymers for controlled drug delivery", edited by Tarcha, CRS Press, Boca Raton, Fla. (1990).

A coating according to the present invention may also comprise plasticizers in the amount of up to 50% and up to 5% of such additives as leveling agents, antifoamants, and the like. These additives are per se well-known in the polymer and coating arts.

The cellulose acetate acetoacetate ester (or the corresponding propionate or butyryl acetoacetate esters) can be made into waterborne coatings by dissolving them, by way of example, in dilute aqueous basic solutions such as 10% aqueous ammonia solutions, 0.1N $NaHCO_3$ solutions, having, again by way of example, 0.5N mixed cellulose acetoacetate ester concentration. Such solutions can then be applied via a fluid bed coater onto a solid substrate, such as particles, pellets, beads, and tablets. Such coating processes are per se known to the skilled artisan.

Accordingly, by varying the exact identity of the ester OR, the degree of substitution for x and y and the total degree of substitution x+y, the molecular weight of the cellulose acetoacetate ester, or n, the pH at which the cellulose acetoacetate ester according to the present invention will be soluble and/or dissolve can be varied between about pH>7 to highly alkaline conditions. In other words, the cellulose acetoacetate ester can be made to dissolve at pH=7.5, 8, 8.5, 9, 10, or 11, and not before, given the appropriate selection of the aforementioned parameters. Thus, the cellulose acetoacetate esters according to the present invention can be designed to have a characteristic pH at 7.8, 8.3, 9.5, etc. By "characteristic pH" is meant that the material will dissolve at that pH, and not before, as alkalinity is increased.

Specific Examples of coatings according to the present invention

The following examples are meant to illustrate preferred embodiments of the present invention, but should not be interpreted as a limitation thereon. Numerous modifications and variations will be evident to skilled practitioners of the art, and it is to be understood that within the scope of the appended claims, the invention may be practiced otherwise than as specifically described herein.

EXAMPLE 1

Cellulose acetate acetoacetate (C(AA)A) with x equal to about 1.4 to about 1.6, y equal to about 1.0 to about 1.2, and a total degree of substitution (x+y) of about 2.6 is prepared. The characteristic pH of this material is about 9.5.

Urea prills are coated as follows. 30 g. of the C(AA)A is dissolved in a 270 g. of a 90:10 acetone:water solution, along with 7.5 g. of triethyl citrate plasticizer. Using this solution, 200 g. urea prills are coated using a commercial lab coater with a coating time of 45 min. The coating weight of coated urea particles is about 11% by weight.

EXAMPLE 2

Release of urea from the coated prills of Example 1 is determined at pH=7 and pH=11 using sodium phosphate buffer solutions. A 1 g. sample of coated prills, having a coating weight of about 11% by weight, is extracted in 500 ml of buffer solution. Three samples are prepared at each pH value. At periodic intervals, a 0.25 ml aliquot is removed and assayed on a COBAS BIO analyzer using SIGMA BUN (RATE) reagent and Sigma urea standards as controls. The samples are agitated periodically by inverting the flask. A blank is also prepared by adding 0.15 g. of the identical C(AA)A to 500 ml pH 11=buffer.

The results are shown in FIG. 1. It is known that urea is highly soluble in water, with one gram of urea dissolving in one ml of water (Merck Index, 3rd Ed.(1983)). However, in pH=7 buffer solution, the release of urea from coated particles does not exceed 5% in 6 hours of extraction time, as shown in lowest curve of FIG. 1. No measurable C(AA)A was detected in the buffer solutions.

When coated urea particles were extracted in pH=11 buffer solution, urea becomes detectable when C(AA)A coating dissolved, as shown in the upper two curves of FIG. 1. When about 5% of the C(AA)A coating (middle curve) is detected in solution after about 60 minutes the release of urea into the buffer solution reaches about 95% of the total (upper curve).

This example demonstrates the novel pH-dependent dissolution characteristics of C(AA)A in buffer solution, and its application for protection of water-sensitive hygroscopic or water-soluble materials through microencapsulation.

EXAMPLE 3

This example illustrates the use of a C(AA)A according to the present invention to encapsulate enzyme-containing particles starting from the enzyme concentrate in liquid form.

Cellulose acetate acetoacetate (C(AA)A) with x equal to about 1.0 to about 1.2, y equal to about 1.2 to about 1.4, and a total degree of substitution (x+y) of about 2.6 is prepared. The characteristic pH of this material is about 8.5.

A protease concentrate containing greater than 10% solids is warmed to about 30° C. and commercially available PEG 400 (polyethylene glycol) and sodium sulfate are added to give a final solution composition of about 10% PEG 400 and 14% sodium sulfate. The solution is mixed for a minimum of 30 minutes at constant temperature and then the phases are separated by passing the liquid through a centrifugal extractor. The light phase containing the protease and PEG 400 is collected, while the heavy phase containing the sodium sulfate is discarded.

Based on the concentration of the extract, protease is added to a preblended mixture of sodium sulfate, PEG 8000, cellulose powder (premixed at a ratio of 4.25:1.00:1.00) and amylase powder. The amount of amylase powder added is optional and dependent on its active concentration. Water is added to the blend to bring the moisture content to about 15%. Temperature is controlled on the blending step to assure that the product temperature does not exceed 25° C.

After about 30 minutes mixing time, the material is fed to an extruder such as Luwa EXD, low shear, radial type extruder, which forces it through a 0.7 mm screen. The noodles formed are collected for further processing. The overflow (unextruded waste) from the extruder can be recycled back into the feed as long as it is sufficiently blended with fresh material from the mixing step. The screen temperature on the extruder will be around 31° C. as long as the moisture content of the feed is in the correct range.

The noodles are fed batch-wise into the marumerizer and processed for a long enough time to round the product to the right particle size. During this rounding step, a mixture of Avicel and $TiO_2$ (60.40 by weight) is added to ensure that no clumping occurs. Total weight gain during this step is typically 10 to 15%.

The material is dried in a fluid bed drier to a final moisture content of less than 2%. The product temperature during the drying process is not allowed to rise above 50° C.

The dried product is sieved between 16 and 40 mesh screens. This material is then coated with C(AA)A coating solution, in the manner similar to Example 1, in a fluid bed coater. The feed solution is sprayed onto the fluidized material while maintaining the bed temperature during this process at 30° to 35° C. The final coating weight on the product is approximately 10 to 15%.

EXAMPLE 4

This example illustrates that liquid enzyme concentrate is absorbed into a carrier and then encapsulated with C(AA)A.

The liquid enzyme concentrates containing single or multiple type of enzymes and additives such as PEG is sprayed onto fluidizing non-prill sugar beads or beads made of inert polymeric materials such as microcrystalline cellulose or inorganic porous particulates in a fluidized bed. After spraying the liquid concentrate completely, the particles are continually dried in the fluid bed coater to a final moisture content of less than 2%. The product temperature during the drying process is kept below 50° C. The coating solution with enzyme-containing C(AA)A is then sprayed onto the enzyme-containing particles, in a manner similar to Example 1.

EXAMPLE 5

This example describes the use of C(AA)A for coating of pharmaceutical solids. 5-ASA tablets are coated with C(AA)A having x equal to about 0.4 to about 0.6, y equal to about 1.6 to about 1.8, and a total degree of substitution of about 2.2. The characteristic pH of this material was about 7.5. The coating conditions are similar to those described in Example 1. These coated tablets will not disintegrate in a buffer at about pH=6.8, but will dissolve at about pH=7.5 or above.

A further preferred embodiment is a coating comprising the acetoacetate ester according to the present invention and a second cellulose material, such as commercially available CAP. C(AA)A according to the present invention and a commercially-available enteric coating polymer CAP is dissolved at a ratio of 1:1 in acetone/water (90/10). Plasticizers may be optionally added to the solution. Pharmaceutical solid substrates such as pellets, tablets, or prills can then coated with the blend. The coated substrate still dissolves at a pH higher than 7.0. The ratio of C(AA)A/CAP can be adjusted to meet the need for specific pH-dependent release profiles.

Thus, the present invention is based on the surprising discovery that certain cellulose acetoacetate esters will remain insoluble in mild (near-neutral) or acidic aqueous solutions, but will be soluble under alkaline conditions. The exact pH at which dissolution occurs can be adjusted by proper design of the ester, as shown in Examples 1, 3, and 5, above. Furthermore, coatings comprising these esters will remain stable to incidental moisture and yet dissolve to release a coated active agent under alkaline conditions, as shown in particular by Example 2 above, and also illustrated by Example 4.

The invention has been described in detail with particular reference to preferred embodiments thereof. However, it will be understood that variations and modifications other than as specifically described herein can be effected within the spirit and scope of the invention. Moreover, all patents and literature references or other publications noted above are incorporated herein by reference for any disclosure pertinent to the practice of this invention.

We claim:

1. A coated substrate comprising a substrate and a coating, said coating comprising a cellulose acetoacetate mixed ester having a total degree of substitution of greater than 1.0, wherein said ester is not crosslinked, said ester being insoluble in acidic or neutral aqueous solution but soluble under alkaline conditions, and having a second ester selected from $C_2$–$C_4$ acyl-containing aliphatic groups; and wherein said substrate is selected from the group consisting of medicaments, nutrients, pesticides, herbicides, laundry products, and mixtures thereof.

2. The coated substrate according to claim 1, wherein said substrate is selected from the group consisting of medicaments, nutrients, and mixtures thereof.

3. The coated substrate according to claim 1, wherein the total degree of substitution is greater than about 1.1.

4. The coated substrate according to claim 1, wherein said substrate is a medicament, the degree of substitution is from about 1.1 to about 2.75, wherein said ester is soluble in aqueous solution at a pH of about 7.5, and not before.

5. A composition comprising at least one active agent and at least one cellulose acetoacetate mixed ester, wherein said at least one cellulose acetoacetate mixed ester is not crosslinked, is insoluble in neutral and acidic aqueous solution but is soluble in alkaline aqueous solution and is represented by the formula:

$$[(C_6H_7O_2)(OR)_x(OR')_y(OH)_{3-x-y}]_n$$

where R is selected from $C_2$–$C_4$ acyl-containing aliphatic groups, and R' is acetoacetyl, x is from about 0.25 to about 2.0, y is from about 0.5 to about 2.75, having a total degree of substitution greater than 1, and n is from about 50 to about 400;

and where said at least one active agent is selected from the group consisting of medicaments, nutrients, cleaning agents, pesticides, herbicides, and mixtures thereof.

6. A composition according to claim 5, said ester having a total degree substitution greater than 1.1 and having a characteristic pH of about 7.5 or greater.

7. A composition according to claim 6, wherein at said at least one active agent is a medicament, said ester having a characteristic pH of about 8.0 or greater.

8. A composition according to claim 7, wherein said at least one medicament is 5-ASA.

9. A composition according to claim 5, wherein said at least one active agents is a catalyst.

10. A composition according to claim 9, wherein said catalyst is an enzyme.

11. An aqueous alkaline solution comprising a cellulose acetoacetate mixed ester having a total degree of substitution of greater than 1.0 and having a second ester selected from $C_2$–$C_4$ acyl-containing aliphatic groups.

12. The aqueous alkaline solution according to claim 11, wherein said cellulose acetoacetate mixed ester has a total degree of substitution of about 1.1 or greater and having a second ester selected from acetyl, propionyl, or butyryl.

13. The aqueous alkaline solution according to claim 12, wherein said cellulose acetoacetate mixed ester is cellulose acetate acetoacetate having a total degree of substitution of 1.1 or greater.

14. The aqueous alkaline solution according to claim 13, wherein said cellulose acetoacetate mixed ester is cellulose acetate acetoacetate having a total degree of substitution of from about 2.2 to about 2.75.

15. The coated substrate according to claim 1, wherein said substrate comprises an medicament.

16. The coated substrate according to claim 15, wherein said substrate comprises 5-ASA.

17. The aqueous alkaline solution according to claim 11, further comprising a medicament.

18. The solution aqueous alkaline solution according to claim 17, further comprising 5-ASA.

* * * * *